(12) United States Patent
Djeu (10) Patent No.: US 7,855,780 B1
(45) Date of Patent: Dec. 21, 2010

(54) COMBINED FIBER-OPTIC ABSORPTION AND EMISSION MEASUREMENT APPARATUS

(75) Inventor: Nicholas Djeu, Tampa, FL (US)

(73) Assignee: University of South Florida, Tampa, FL (US)

( * ) Notice: Subject to any disclaimer, the term of this patent is extended or adjusted under 35 U.S.C. 154(b) by 87 days.

(21) Appl. No.: 12/139,015

(22) Filed: Jun. 13, 2008

Related U.S. Application Data (60) Provisional application No. 60/934,427, filed on Jun. 13, 2007.

(51) Int. Cl.
G01N 21/65 (2006.01)
G01N 21/35 (2006.01)

(52) U.S. Cl. .................. 356/73; 356/301; 250/339.07

(58) Field of Classification Search ............... 356/73, 356/301
See application file for complete search history.

(56) References Cited

U.S. PATENT DOCUMENTS

| | | | |
|---|---|---|---|
| 4,945,245 A | | 7/1990 | Levin |
| 5,293,872 A | * | 3/1994 | Alfano et al. ............ 600/475 |
| 5,404,218 A | | 4/1995 | Nave et al. |
| 5,751,415 A | | 5/1998 | Smith et al. |
| 5,838,843 A | * | 11/1998 | Aose et al. ............... 356/73 |
| 5,841,139 A | | 11/1998 | Sostek et al. |
| 5,889,279 A | | 3/1999 | Couston |
| 6,118,520 A | * | 9/2000 | Harner .................... 356/73 |
| 6,121,616 A | | 9/2000 | Trigg |
| 6,188,812 B1 | | 2/2001 | Kao et al. |
| 6,198,861 B1 | | 3/2001 | Kellar et al. |
| 7,095,502 B2 | | 8/2006 | Lakowicz et al. |

OTHER PUBLICATIONS

Khijwania, S. K.; Gupta, B. D. "Fiber optic evanescent field absorption sensor with high sensitivity and linear dynamic range." Optics Communications. vol. 152. Issue 4-6. pp. 259-262, Jul. 1998.
Marcuse, D. "Launching light into fiber cores from sources located in the cladding." Lightwave Technology. vol. 6. Issue 8. Aug. 1988. pp. 1273-1279.
Woerdeman, Dara L.; Parnas, Richard S. "Model of a fiber-optic evanescent-wave fluorescence sensor." Applied Spectroscopy. vol. 55. Issue 3. Mar. 2001. pp. 331-337.
Lieberman, R.A.; Blyler, L.L.; Cohen, L.G. "A distributed fiber optic sensor based on cladding fluorescence." Lightwave Technology, vol. 8. Issue 2. Feb. 1990. pp. 212-220.

* cited by examiner

*Primary Examiner*—F. L Evans
(74) *Attorney, Agent, or Firm*—Jeremy Spier; Smith & Hopen, P.A.

(57) ABSTRACT

Disclosed is a spectroscopic system having a fiber-optic probe for simultaneous IR and Raman measurement. The probe includes a single strand of optical fiber, such as sapphire which is suitable for IR absorption measurements as far as 4 μm and Raman excitation at wavelengths as short as 300 nm. The probe is immersed in the sample and functions in the evanescent wave mode for both IR absorption and Raman scattering measurements. The sensing system makes possible the synergistic, and simultaneous, analysis of both IR and Raman data in an integrated device.

34 Claims, 7 Drawing Sheets

RAMAN TENSOR COMPONENTS OF SAPPHIRE

| Frequency | Linewidth | $\alpha_{xx}^2$ | $\alpha_{zz}^2$ | $\alpha_{xy}^2$ | $\alpha_{xz}^2$ |
|---|---|---|---|---|---|
| 378.7 cm$^{-1}$ | 2.4 cm$^{-1}$ | 0.0 | 0.0 | 0.0 | 0.24 |
| 417.4 | 2.2 | 1.0 | 1.04 | 0.0 | 0.0 |
| 430.2 | 3.1 | 0.063 | 0.0 | 0.058 | 0.081 |
| 448.7 | 2.2 | 0.060 | 0.0 | 0.055 | 0.0 |
| 576.7 | 3.2 | 0.141 | 0.0 | 0.133 | 0.0 |
| 644.6 | 7.1 | 0.0 | 0.57 | 0.0 | 0.0 |
| 750.0 | 9.5 | 0.53 | 0.0 | 0.57 | 0.0 |

US 7,855,780 B1

COMBINED FIBER-OPTIC ABSORPTION AND EMISSION MEASUREMENT APPARATUS

CROSS REFERENCE TO RELATED APPLICATIONS

This application is a Nonprovisional application of U.S. Provisional Application No. 60/934,427 filed Jun. 13, 2007, which is incorporated herein by reference.

BACKGROUND OF THE INVENTION

The chemical and petrochemical industries, in particular, are major consumers of energy in the generation and processing of their products. The optimization of the existing processes requires an improved ability to monitor, among other parameters, the chemical composition of the reactor streams. The sensors needed to provide this information must be sufficiently robust so that they can withstand harsh chemicals at high temperatures and, in some situations, function in the presence of solids. Optical techniques, especially IR and Raman spectroscopies, have always played an important role in process control in the chemical industry. IR and Raman measurements provide complementary information on the chemical composition of a reactor stream, in so far as the terminal vibrational levels of the molecules accessed by the two types of transitions do not overlap in general. In other words, bands that are strong in IR absorption are typically weak in Raman scattering, and vice versa. Furthermore, the instrumentations for these two kinds of spectroscopy are vastly different and separate probes must be used for their respective implementations.

Fiber-optic absorption sensors in the near-IR first made their way into chemical plants in the 1990's. In a typical system light is guided by an optical fiber to a probe, where it is collimated and sent out a window. After traversing a gap through which the reactor stream flows, it is passed through a second window and refocused into a second fiber which carries it to the detector. These probes are now widely used in the observation of overtone and combination bands as part of process control in the chemical industry.

An evanescent wave mid-IR absorption sensor between 2.5 µm and 11.5 µm has been demonstrated using a chalcogenide glass fiber (see J. S. Sanghera, F. H. Kung, P. C. Pureza, V. Q. Nguyen, R. E. Miklos, and I. D. Aggarwal, "Infrared evanescent-absorption spectroscopy with chalcogenide glass fibers," *Appl. Opt.* 33, 6315-(1994)).

Fiber-optic Raman probes generally use one delivery fiber to guide the excitation light to the sample and one or more collection fibers to carry the Raman scattered light to the spectral analyzer. Note that this geometry is in contrast to the one described earlier for the conventional IR absorption probe, wherein electromagnetic energy passes through the sample reactor as well as the evanescent wave absorption probe.

What is needed, however, is a fiber-optic Raman probe capable of the simultaneous determination of IR and Raman spectral features to provide complimentary information on the chemical system being analyzed.

SUMMARY OF INVENTION

The invention includes a fiber-optic probe capable of simultaneous IR and Raman measurement. The probe includes a single strand of optical fiber, such as sapphire which is suitable for IR absorption measurements as far as 4 µm and Raman excitation at wavelengths as short as 300 nm. In one embodiment, the probe is side-coupled to the sample and functions in the evanescent wave mode for both IR absorption and Raman scattering measurements. The inventive sensing system makes possible the synergistic, and simultaneous, analysis of both IR and Raman data in an integrated device.

In an illustrative embodiment, the invention includes a spectroscopic system having a fiber-optic probe which is immersed in a fluid sample. A first light and second light source are optically coupled to the fiber-optic probe. In non-exclusively alternate embodiments, the fiber-optic probe is tapered (being thicker at is ends), has a diameter smaller than about 100 µm, is helical, and/or is a sapphire fiber.

The first light source is a laser which emits light having an excitation wavelength, light having a wavelength of about 532 nm, monochromatic light, near infrared light, ultraviolet light and/or near ultraviolet light. The first spectral analyzer is optically coupled to the fiber-optic probe and measures light from the first light source that is spectrally dispersed by the sample through the fiber-optic probe. In one embodiment, the first spectral analyzer measures Raman scattered light emanating from the sample through the fiber-optic probe.

The second light source is a laser which emits light having a continuously tunable wavelength, incoherent light, near infrared light and/or infrared light. A second spectral analyzer is optically coupled to the fiber-optic probe and measures light from the second light source that is spectrally dispersed by the sample through the fiber-optic probe. In an illustrative embodiment, the second spectral analyzer measures the attenuated light emanating from the sample, through the fiber-optic probe, as a result of the evanescent absorption in the infrared wavelengths. In one arrangement, the second spectral analyzer measures infrared light emanating from the sample through the second end of the fiber-optic probe.

The spectroscopic system can also include optical assemblies for receiving and conveying optical signals, thereby establishing optical communication between the components of the system. In one embodiment, for example, a first optical assembly provides optical communication between at least one light source and the fiber-optic probe and a second optical assembly provides optical communication between at least one spectral analyzer and the fiber-optic probe. In a first embodiment, the first optical assembly is in optical communication between the first light source, the second light source and the first end of the fiber-optic probe. In a non-mutually exclusive embodiment, the first optical assembly is in optical communication between at least one light source, the fiber-optic probe as well as the first spectral analyzer. The first optical assembly can be placed in optical communication between at least one light source and the first end of the fiber-optic probe. In another embodiment, the second optical assembly is in optical communication between the second spectral analyzer and the second end of the fiber-optic probe.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The invention includes a spectroscopic system and fiber-optic probe capable of simultaneous IR and Raman measurement. In one embodiment, the probe includes a single strand of optical fiber, such as sapphire which is suitable for IR absorption measurements as far as 4 μm and Raman excitation at wavelengths as short as 300 nm. The fiber-optic probe functions in the evanescent wave mode for both IR absorption and Raman scattering measurements. The inventive sensing system makes possible the synergistic, and simultaneous, analysis of both IR and Raman data in an integrated device. In another embodiment, the probe is a side-coupled probe allowing it to collect more signal than the end-coupled probe of the prior art. By coiling the fiber into a tight helical shape, the evanescent wave absorption coefficient is significantly increased allowing quantitative measurements on overtone and combination bands in liquids. At the same time, information on the strong fundamental bands in the 3-4 μm region can be gained by analyzing the shapes of the wings of their absorption profiles.

Evanescent Wave Absorption and Emission Sensing

Evanescent wave absorption is based on the principle that when a core-only optical fiber with refractive index $n_c$ is immersed in a sample substance with refractive index $n_s < n_c$, the sample acts as a cladding. When optical radiation is passed through the optical fiber, a small fraction of the lightwave energy being guided by the fiber resides in the cladding (sample). If the sample exhibits an absorption coefficient $\alpha_s$ at the wavelength of the propagating light, it will be attenuated with an evanescent wave absorption coefficient $\alpha = \eta \alpha_s$, where $\eta$ is the fraction of light energy in the form of the evanescent wave. The value of $\alpha$ is mode-dependent, increasing with the order of the mode, becoming largest for those modes near cutoff. For the latter, the evanescent field can penetrate into the medium surrounding the fiber to depths on the order of a wavelength.

Evanescent wave emission sensing seems like an oxymoron, since in the ray picture any light from the cladding refracted into the fiber will diminish a little every time it undergoes a reflection at the fiber-cladding interface. Thus, it would appear that light sources in the cladding cannot give rise to any guided wave in the fiber. However, this is not the case when the problem is analyzed with the wave treatment. In that picture, a light source in the cladding can induce a bound mode in the fiber through its spatial overlap with the mode's evanescent field.

Marcuse (see Marcuse, D: "Launching light into fiber cores from sources located in the cladding," Journal of Lightwave Technology. Vol. 6, no. 8, pp. 1273-1279. 1988) performed numerical calculations for the case where the cladding light sources are confined in a circular layer near the fiber's surface which is thin compared to the penetration depth of the evanescent fields. Marcuse addressed the problem of the efficiency of light injection into the cores of optical fibers from sources that are located in its cladding region. Marcuse used a model consisting of a light collecting fiber with sources in its cladding which is connected to an "attached fiber" with fixed numerical aperture that guides the collected light to a detector. He considered light injection into positively guiding fibers (core index larger than cladding index) as well as leaky fibers (core index less than cladding index) and concluded that positively guiding fibers, if they are made long enough, can collect more light than leaky fibers.

Marcuse reported results for fiber V parameters ranging from 0 to 30 and also for the case of V=300. The V parameter is defined by $$V = (2\pi a/\lambda)[(n_c)^2 - (n_{cl})^2]^{1/2} \quad (1)$$

where a is the core radius, $n_{cl}$ is the refractive index of the cladding, and $\lambda$ is the vacuum wavelength. It was found that the ratio of the power coupled into the fiber to the total power radiated by the thin layer increases from 0 at V=0 to $2 \times 10^{-2}$ at V=30, and is 0.6 at V=300.

To estimate the Raman power generated by the evanescent field of the excitation lightwave, one must know what fraction of the latter propagates in the cladding. For that purpose we follow the procedure developed by Katz et al. [2]. According to their model, which is based on the ray picture and accounts for cladding loss (either through absorption or scattering) by using a complex refractive index, the fraction of energy which propagates as evanescent wave is given by $$\eta = \frac{\lambda \theta_m^2}{32\pi a}(M_s + M_p) \quad (2)$$

where $\theta_m$ is the maximum angle that the rays in the fiber make with respect to the fiber axis and $$M_s = \frac{4n_{cl}}{n_c^2[1 - (n_{cl}/n_c)^2]^{3/2}} \quad (3)$$

$$M_p = M_s[2 - (n_{cl}/n_c)^2] \quad (4)$$

In deriving Eq. (2), it was assumed that there is a uniform angular distribution of power among the rays propagating at different angles. It is seen that the fractional power residing outside the fiber depends inversely on the fiber radius and quadratically on the angular range of the rays within the fiber.

Fiber-Optic Probe

Figure 4:
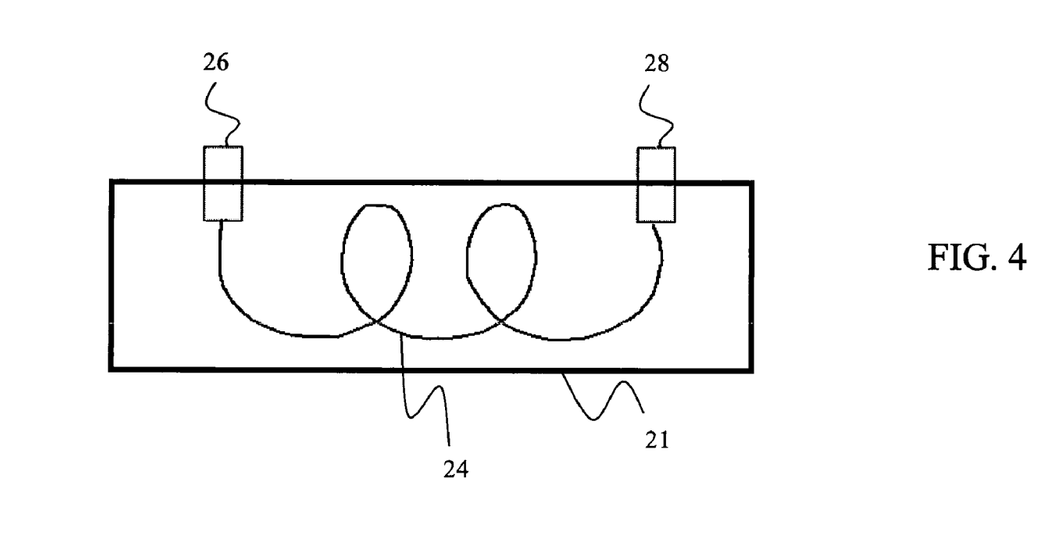
FIG. 4 is a diagram of an illustrative orientation of the probe within a sample.

A schematic of an illustrative orientation of the fiber optic probe is shown in FIG. 4. Perforated body 21 provides protection for fiber-optic fiber-optic probe 24 while allowing the free movement of the sample. First probe connection 26 is connected to one end of fiber-optic probe 24 and second probe connection 28 is disposed on the opposite end of fiber-optic probe 24. In side-coupled embodiments, first and second probe connections are arranged such that they are substantially perpendicular to the longitudinal axis of fiber-optic fiber-optic probe 24. Fiber-optic probe 24, in one embodiment, includes a single helical sapphire fiber. Here, the ends of fiber-optic probe 24 are in air rather than the sample medium.

In end-coupled fiber-optic Raman probes based on standard silica fibers, a filter is used in front of the collecting fiber to block any scattered excitation laser light, which would otherwise induce an interfering Raman signal upon passage through the collecting fiber. The end-coupled Raman signal is independent of the length of the fiber, assuming negligible loss of the excitation light in its propagation through the fiber.

In the side-coupled approach, the excitation of Raman lines in the fiber is inevitable. This effect is believed to depend on the refractive index of the fluid in which the fiber is immersed as well as the power of the excitation source. Methods of nulling these fiber Raman lines are discussed below. The side-coupled Raman signal collected by the fiber scales linearly with the interaction length. The sapphire fiber, of a one embodiment, is less than 1 m long to prevent measurable loss over distances.

In one embodiment, the probe hase flared ends. For a given fiber diameter, to achieve maximum side-coupled Raman emission, the launch numerical aperture should be as large as possible subject to the excitation lightwave still being guided in the interaction region. This may effect performance for fluids with a low refractive index in the case of a sapphire fiber. To remedy the situation, the fiber includes an increasing taper at the launching end, which effectively increases the angle of the rays as the fiber is tapered down.

The probe is coiled in one embodiment for the purpose of creating as compact a probe as possible. More importantly, coiling the fiber increases the evanescent wave absorption coefficient. Since the Raman emission is produced by the evanescent field of the excitation lightwave, the collected signal per unit length of the fiber increases.

Side-Coupled Fiber Probe Performance

Figure 1:
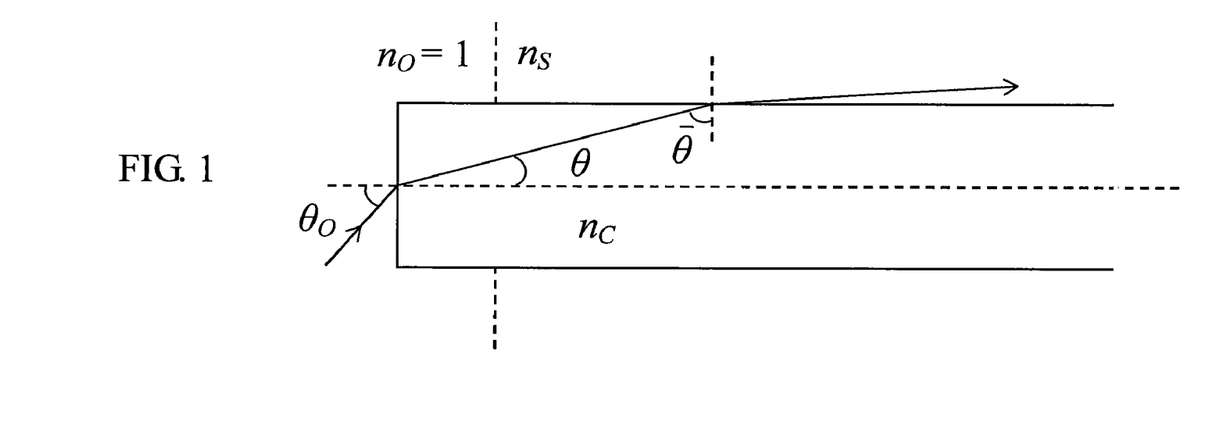
FIG. 1 is a diagram of a fiber-optic strand showing the angle of refraction therein.

Sapphire fibers have no cladding in their normal state. Therefore, whatever they are placed in acts as the cladding. In one embodiment, the ends of the fiber are in air, rather than the sample medium, with refractive index $n_o=1$. The refractive index of sapphire at 532 nm is approximately n=1.77. The refractive index of the sample is taken to be $n_s=1.50$. Using the notations for the various angles indicated in FIG. 1, we see that $$\theta_o = \sin^{-1}(n_c \sin \theta) \quad (5)$$

and that the maximum value for $\theta$ is obtained when $\bar{\theta}$ is the critical angle, i.e., $$\theta_m = \frac{\pi}{2} - \sin^{-1}(n_s/n_c) \quad (6)$$

Using the values for the refractive indices given above, $\theta_m = 32°$. This implies a corresponding $\theta_o$ of 70°.

The sapphire fibers of the illustrative embodiment have a diameter of 60 μm. With $\theta_n = 32°$ it can be determined from Eqs. (2)-(4) that $\eta = 1.6 \times 10^{-3}$. Thus, letting the powers of the excitation light in the fiber and in the Raman medium be P and $P_s$ respectively, for a 532 nm excitation wavelength in a 60 μm sapphire fiber immersed in a sample with $n_s = 1.50$ with all the bound modes excited $$P_s = 1.6 \times 10^{-3} P \quad (7)$$

Assuming that the evanescent wave has a uniform amplitude in an annular region with an inner radius a and an outer radius $a+d_p$, where $d_p$ is an effective penetration depth, and zero amplitude beyond that, one obtains for the intensity in the annular region $$I_s = \frac{P_s}{2\pi a d_p} \quad (8)$$

Then the Raman power generated over a length l of the fiber is $$P_s^R = I_s(2\pi a d_p l) \rho \sigma_R = l \rho \sigma_R P_s \quad (9)$$

where ρ is the molecular number density in the Raman medium and $\sigma_R$ is the Raman cross section.

Finally, the V parameter for the 60 μm fiber in the Raman medium is calculated from Eq. (1) to be 314, which is sufficiently close to 300 to justify the use of the back-coupling efficiency of 0.6 obtained by Marcuse for the latter value. Then the Raman power back-coupled into the fiber is $$P^R = 0.6 P_s^R \quad (10)$$

Combining Eqs. (7), (9), and (10), we obtain $$P^R = 1.0 \times 10^{-3} l \rho \sigma_R P \quad (11)$$

In the calculations performed by Marcuse, the light source in the cladding was assumed to be infinitesimally thin. In fact, the evanescent field of the excitation light extends a distance of order $d_p$ into the Raman medium. This would tend to decrease the amount of Raman power back-coupled into the fiber. On the other hand, Marcuse assumed that the cladding light source emits isotropically. In fact, Raman emission peaks in a plane containing the propagation vector. This has the effect of increasing the back-coupling efficiency.

End-Coupled Fiber Probe Performance

Figure 2:
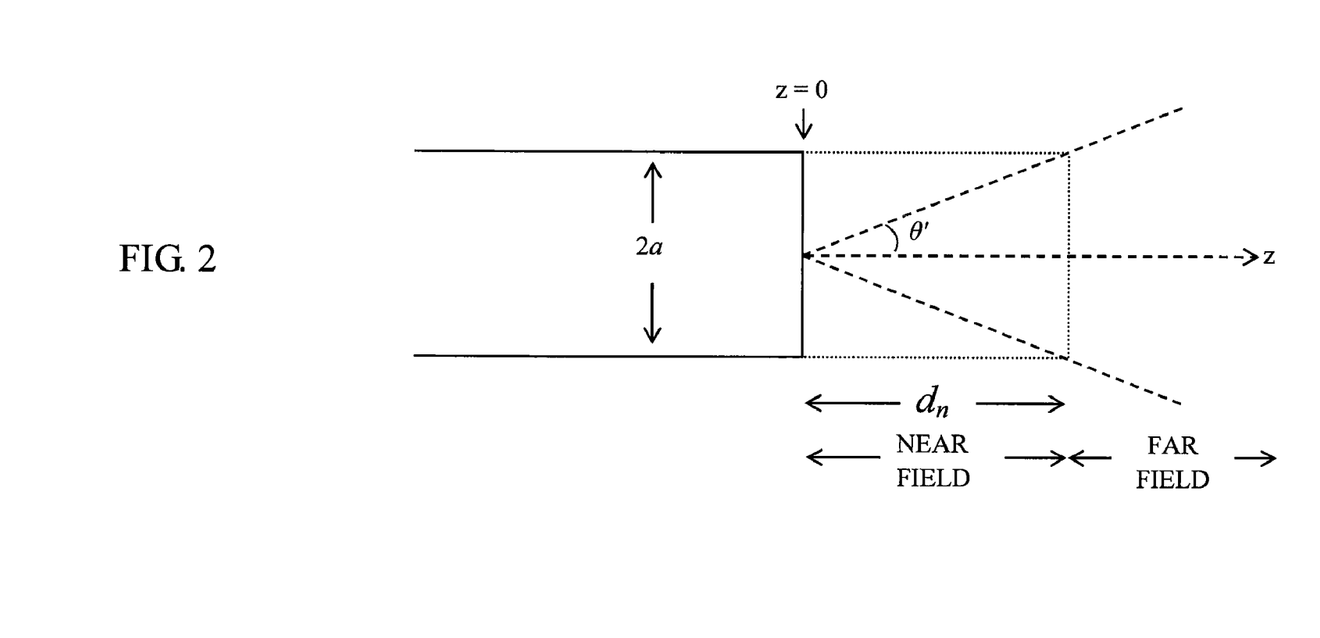
FIG. 2 is a diagram showing the half angle for a beam emerging from a fiber (θ') and the fiber axis (the z axis), with the fiber end positioned in the z=0 plane.

Next we turn to an estimate of the Raman power obtainable in a conventional (end-coupled) fiber-optic probe. To simplify matters, we will analyze the problem for a single fiber used for both excitation and signal collection, instead of two separate fibers as employed in actual Raman probes. This provides an overestimate, as the geometry is most favorable for the case of a single fiber. These calculation take the half angle for the beam emerging from the fiber to be θ' and set the fiber axis as the z axis, with the fiber end positioned in the z=0 plane, as shown in FIG. 2. Since the refractive index of the silica fiber is very close to that for the assumed Raman medium, θ' is essentially equal to the maximum angle of the guided rays inside the fiber. We divide the emitting region into a near field zone with length $d_o$ and a far field zone beyond $d_n$, as shown in FIG. 2. Then in the paraxial approximation $$d_n = \frac{a}{\theta'} \quad (12)$$

For any source point lying on the z axis in the near field, the solid angle of emission that will result in guided rays is $\pi \theta'^2$ str. The solid angle decreases for points not on the z axis. The intensity of the excitation light in the near field is $P/(\pi a^2)$. Thus, the total collected Raman power from the near field, taking its volume to be $\pi a^3/\theta'$, has an upper bound of $$P_{nf}^R = a \theta' \rho \sigma_R P/4 \quad (13)$$

For a source point lying on the z axis in the far field, the solid angle subtended by the fiber end is $\pi a^2/z^2$. For points away from the axis in the same z plane it is smaller, both because the distance from the fiber end becomes larger and because the fiber end area "seen" by the source point becomes smaller. The intensity of excitation light in the far field is $P/(\pi z^2 \theta'^2)$. Thus, the far field contribution to the Raman signal is at most $$P_{ff}^R = \int_{a/\theta'}^{\infty} \frac{a^2}{4z^2} \rho \sigma_R P dz = \frac{1}{4} a\theta' \rho \sigma_R P \qquad (14)$$

and the total collected Raman power from the end is at most $$P_e^R = a\theta' \rho \sigma_R P/2 \qquad (15)$$

Comparison of Side-Coupled and End-Coupled Fiber Probe Performance

Comparing Eqs. (11) and (15), we see that the evanescent wave sapphire fiber Raman probe will collect more signal than an end-coupled fiber-optic Raman probe when l>5000'a. In a typical commercial Raman probe, the collecting fiber has a diameter of 200 μm and a numerical aperture of 0.48. The latter translates into a θ' of 0.33 rad. Thus, an interaction length of 1.7 cm is sufficient under the assumed conditions to produce an evanescent wave Raman probe with the same signal collection efficiency as and end-coupled fiber-optic probe. If $\theta_m$ is decreased, i.e., only the lower order modes are excited, the required length for comparable performance is increased.

Raman Scattering from Sapphire Fiber vs. Sample

In the evanescent wave Raman sensing scheme it is inevitable that the Raman emission from the fiber itself will also be detected. Methods are described below whereby the Raman lines (emissions) from the sapphire fiber are zeroed out. The intensity of the fiber Raman lines will depend on the refractive index of the cladding (i.e., the sample) as well as on the power of the excitation light.

Of all the Raman emission induced in the fiber, only the part emitted in a small cone along the axial direction will be collected. Using logic similar to that used in the estimate of Raman power collected from the near field zone in the end-coupled probe, above, the Raman power from the fiber that will be detected (assuming isotropic emission) should be no more than $$P_f^R = \left(\frac{\pi}{2} - \sin^{-1}(n_s/n_c)\right)^2 l\rho' \sigma_R' P/4 \qquad (16)$$

where $\sigma_R'$ is the Raman cross section and $\rho'$ is the number of unit cells per unit volume for sapphire. For the assumed value of $n_s=1.50$ we find that $$P_f^R = 7.8 \times 10^{-2} l\rho' \sigma_R' P \qquad (17)$$

Comparing this with Eq. (11), we see that the intensity of a Raman line from the sapphire fiber can be expected to be about 2 orders of magnitude larger than that from the sample for $\sigma_R' = \sigma_R$.

Figure 9:
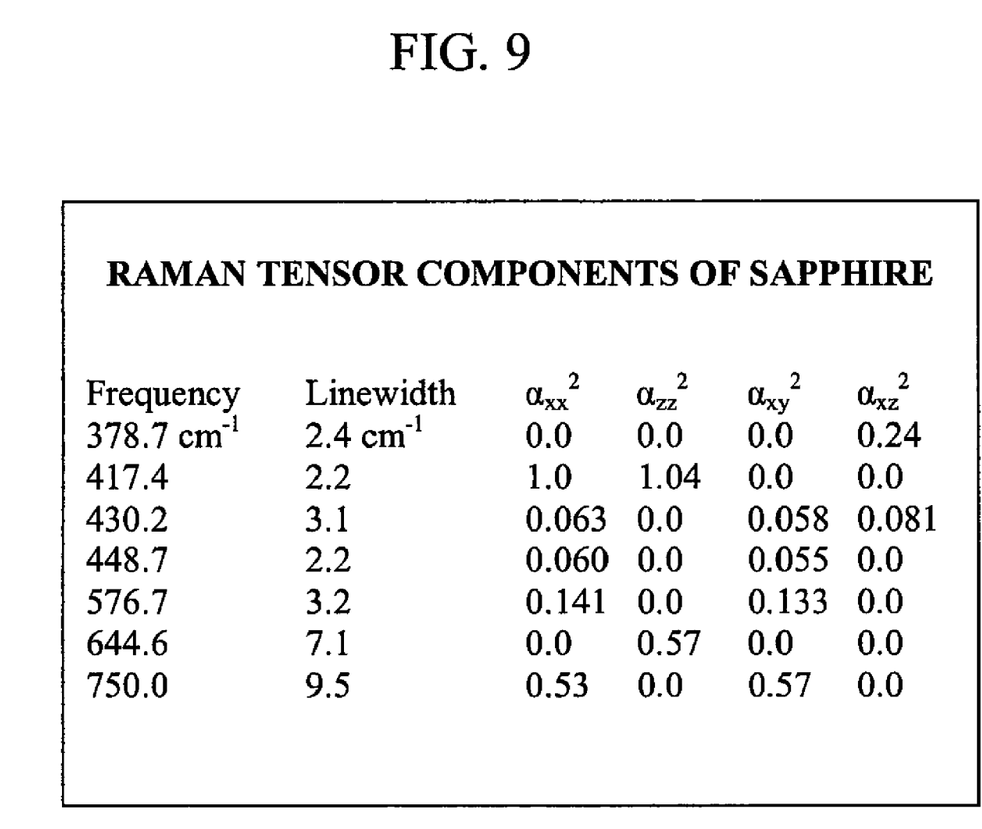
FIG. 9 is a table of the tensor components for all the Raman lines in sapphire, along with their positions and linewidths.

Fortunately, the Raman cross sections in sapphire are relatively small. For the strongest line at 417.4 cm$^{-1}$ the differential cross section is only $1.59 \times 10^{-30}$ cm$^2$/str-unit cell at 514.5 nm, which is about an order of magnitude smaller than the stronger Raman lines in liquids. The tensor components for all the Raman lines in sapphire, along with their positions and linewidths, are shown in FIG. 9. In this table all the $\alpha^2$ values have been normalized to $\alpha^2_{xx}$. These elements are proportional to the differential Raman cross sections, which are in turn proportional to the Raman cross sections used in our analysis. Since the sapphire fiber is oriented in the z direction, the only elements to be addressed are $\alpha^2_{xx}$ and $\alpha^2_{xy}$. Thus, it can be concluded that the main interference from the sapphire fiber will be from the 417.4 cm$^{-1}$ and 750.0 cm$^{-1}$ lines.

Signal Collection from Tapered Fibers

For a fiber with varying diameter, the angle any given ray makes relative to the fiber axis changes with position along the fiber. The relationship is given by $$a(z')\sin\theta(z') = a(z)\sin\theta(z) \qquad (18)$$

That is, the angle varies approximately inversely with the fiber radius.

The large refractive index of the sapphire fiber relative to almost all liquids is an advantage in that the detected Raman signal will not change significantly with small variations in the sample's index caused by changes in temperature or composition. The rays which make the largest contribution to the process in both the excitation step and the collection step, however, are the large-angle rays. For a typical liquid with $n_s=1.4$ these rays are totally reflected at the fiber end. This effect is attenuated by using a fiber which is tapered up to a larger diameter at the end.

Benzene, for example, has a refractive index of 1.50 and a differential Raman cross section of $2.6 \times 10^{-29}$ cm$^2$/str-molecule for the 992 cm$^{-1}$ line for 514.5 nm excitation. For $n_s=1.50$ one calculates a maximum internal ray angle of $\theta_m=32°$. Thus, an impossibly high numerical aperture of 0.94 is needed to efficiently excite as well as collect the Raman emission. In one embodiment, however, the fiber taper is 2:1 (that is a 60 μm sapphire fiber with the coupling end tapered up to 120 μm). In the 120 μm end section, $\theta_m$ is reduced to a value of 15°. Thus, a manageable numerical aperture of 0.47 for the coupling lens will suffice.

For numerical apertures less than 0.47 the Raman signal will decrease and for larger numerical apertures it will also decrease from overfilling. A variable iris between the lens and the fiber produces any desired smaller launch/collection angle.

Effect of Coiling the Fiber

Figure 3:
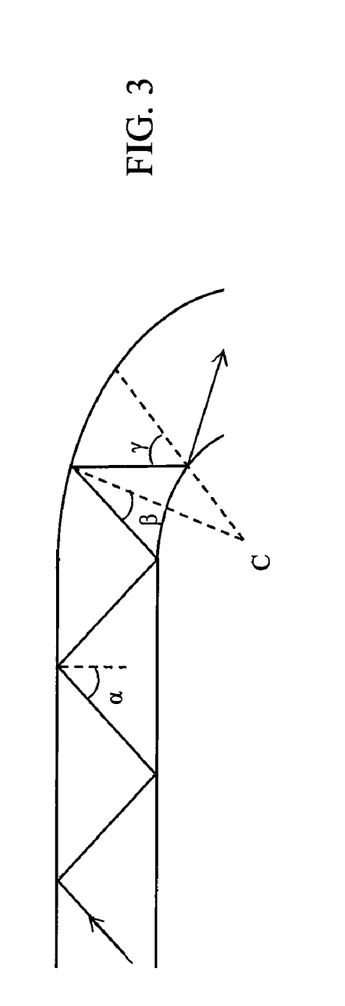
FIG. 3 is a diagram showing the path of a meridional ray lying in the plane of curvature of a fiber.

Evanescent wave absorption can be enhanced by coiling the fiber. The basis for this effect is illustrated in FIG. 3, in which the path of a meridional ray lying in the plane of curvature of the fiber is shown. The center of curvature is denoted by the point C in the figure. The ray makes an angle α with respect to the normal to the fiber surface in the straight section. Upon entering the curved section it is seen that the angle at the outer surface, β, is smaller than α. At the same time, the angle at the inner surface, γ, is larger than α. It is also not difficult to see that for sufficiently large α and small radius, the ray may never touch the inner surface. Since the evanescent wave penetrates deeper into the cladding when the ray makes a smaller angle with respect to the surface normal, interaction with the sample is increased at the outer surface. This effect was first exploited in evanescent wave absorption studies with clad silica fibers. In the latter probes a short length of cladding is removed to expose the core to the probed medium. Since the cladding index is larger than that of most liquids, rays which are close to having the critical angle in the clad region are no longer so in the immersed core-only region when the fiber is kept straight. Coiling the fiber remedied the situation, and large enhancements in evanescent wave absorption were found.

In the case of the sapphire fiber, however, the situation is different in that the cladding in the straight portion is the same sample medium. There is significant enhancement in evanescent wave absorption in the IR when the sapphire fiber is coiled. It is believed that the explanation lies in the fact that skew rays, which constitute the vast majority in a fiber, also follow more favorable paths, although not easily shown pictorially. To the extent that coiling appears to increase the fraction of optical power propagating outside the fiber core, it also increases the Raman power collected per unit length of the fiber.

It is also clear from FIG. 3 that rays which propagate with angles close to the maximum with respect to the fiber axis in the straight section are no longer guided in the curved portion. That is, they will not undergo total internal reflection at the outer surface and will be substantially lost after a number of bounces. This in turn means that the power available for exciting Raman emission from the sample becomes less and less as the excitation lightwave propagates down the fiber. Numerical calculations have shown that, unlike other forms of fiber loss, it does not have an exponential dependence on the length of the bent fiber.

Nulling of Fiber Raman Lines

With a 2-to-1 tapered sapphire fiber it is possible to have optimized performance of the Raman probe in a medium with refractive index as low as 1.11. While no liquid has such a small index, the values of index to be encountered can be expected to vary by as much as 0.3 from one application to another. It would be desirable to have a probe which can null out the Raman signal from the sapphire fiber itself for arbitrary values of the sample's refractive index.

Therefore, the invention includes a built-in means of determining the samples refractive index. This is achieved by correlating the refractive index of the sample medium with transmission of the excitation light through the fiber. If the coupling lens (L2, FIG. 8) is configured to have a numerical aperture at least as large as that required for exciting all the modes for the smallest anticipated sample index, some of the light will be lost for samples with higher indices, causing a decrease in the transmitted power. The input lens must have a sufficiently large numerical aperture. Transmission of 532 nm light through the coiled fiber is measured with a sample cell filled with a number of liquids with refractive indices ranging from 1.33 to 1.63.

Integrated Sensing System

While the following examples depict a dual IR/Raman sensor, the inventive system is also capable of functioning as an IR/fluorescence analyzer. A typical Raman cross section is many orders of magnitude smaller than that for an electronic transition. Thus, induced emission will be readily detectable even for an excited electronic state with very low fluorescence efficiency. Therefore, the invention also includes the combination of IR absorption and visible/UV fluorescence.

Example I

The inventive sensing system of the illustrative embodiment comprises an IR subsystem and a Raman subsystem. In alternate embodiments the Raman subsystem is replaced and or combined with a visible spectrum subsystem, near-IR subsystem, ultraviolet subsystem. In the illustrative embodiments shown below transmission of light between any two points on the optical platform is achieved via free space propagation. One of ordinary skill in the art, however, will appreciate that propagation can be achieved through fiber-optic cables with the optical devices discussed below replaced with appropriate devices for use with same.

Infrared Subsystem

Figure 5:
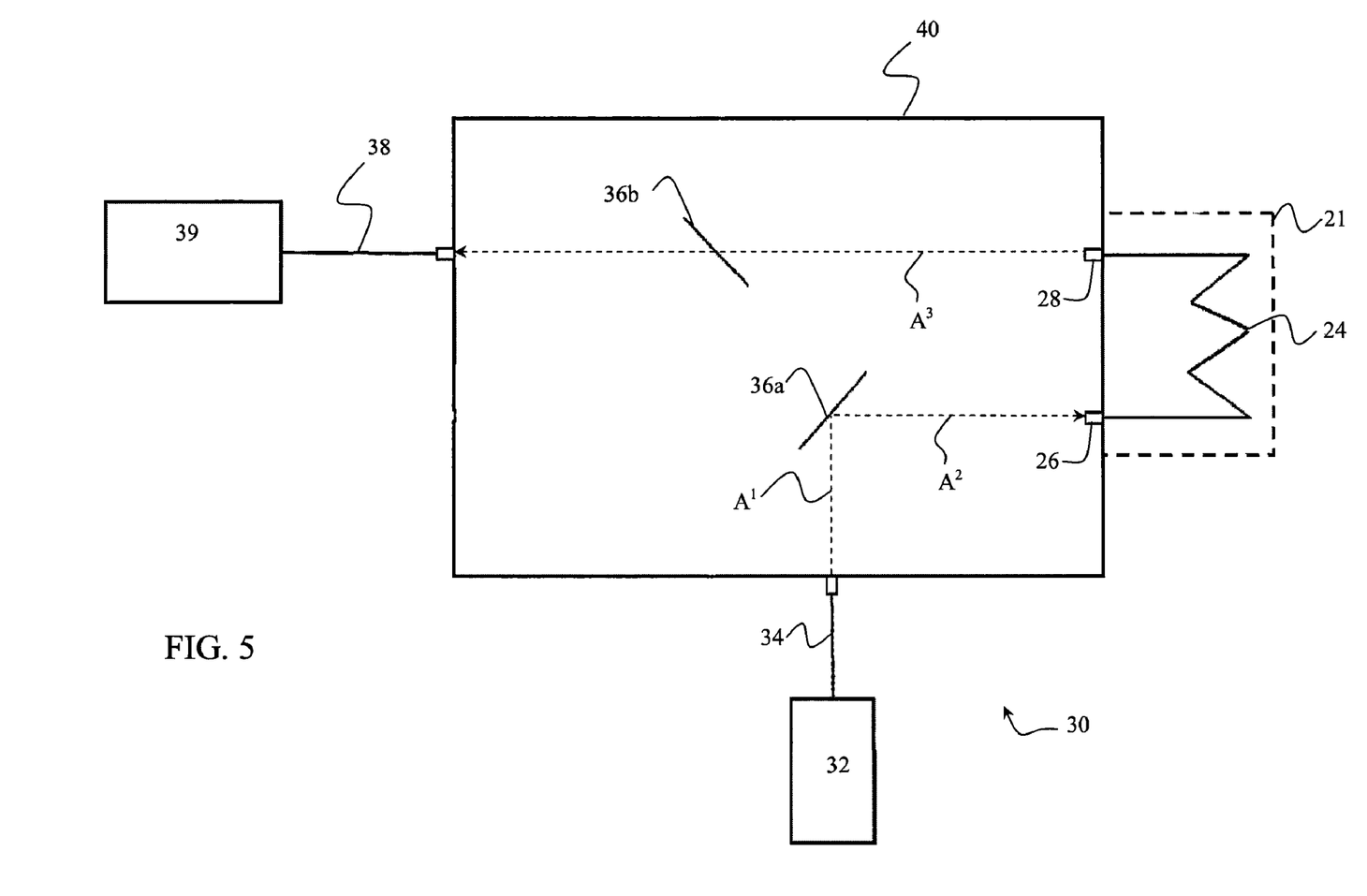
FIG. 5 is a diagram of the infrared subsystem of an illustrative sensing system.

A schematic of the IR subsystem (30) is shown in FIG. 5 wherein IR subsystem 30 comprises fiber-optic probe 24, IR source 32, optical platform 40 and IR spectrometer 39. Optical platform 40 is operatively coupled to IR source 32 through IR source cable 34. Optical platform 40 is operatively couple to fiber-optic probe 24 in sample cell 20 through first probe connection 26 and second probe connection 28. Optical platform 40 is operatively coupled to IR spectrometer 39 through IR spectrometer cable 38. IR source cable 34 and IR spectrometer cable 38, in a preferred embodiment, each comprise a fluoride glass fiber.

IR subsystem 30 further comprises first optical device 36a and second optical device 36b. First optical device 36a is disposed between IR source 32 and first probe connection 26. Second optical device 36b is disposed between second probe connection 28 and IR spectrometer 39. Optical devices 36a and 36b can be any device which controls an optical path of travel. For example, in one embodiment, optical device 36a is a dichroic device wich reflects infrared light but transmits visible light (including Raman scattered light) and optical device 36b is a dichroic device wich transmits infrared light but reflects visible light (including Raman scattered light) to a detector (not shown) for monitoring the system as well as reference purposes. Optical devices 36a and/or 36b can also be a beam splitter, beam combiner or combination thereof.

In operation, IR source 32 emits infrared electromagnetic energy (IR light) having an excitation wavelength through IR source cable 34 into optical platform 40. The IR light travels along path $A^1$ until it contacts first optical device 36a and is redirected along path $A^2$, thereby defining a first optical path, through first probe connection 26. The IR light then travels through fiber-optic probe 24, which is immersed in the sample, and exits at second probe connection 28. Upon exiting second probe connection 28, the IR light is collimated and travels along optical path $A^3$ through second optical device 36b and directed to IR spectrometer 39 through IR spectrometer cable 38. The output from IR spectrometer 39 is fed into an electronic processor for analysis.

Raman Subsystem

Figure 6:
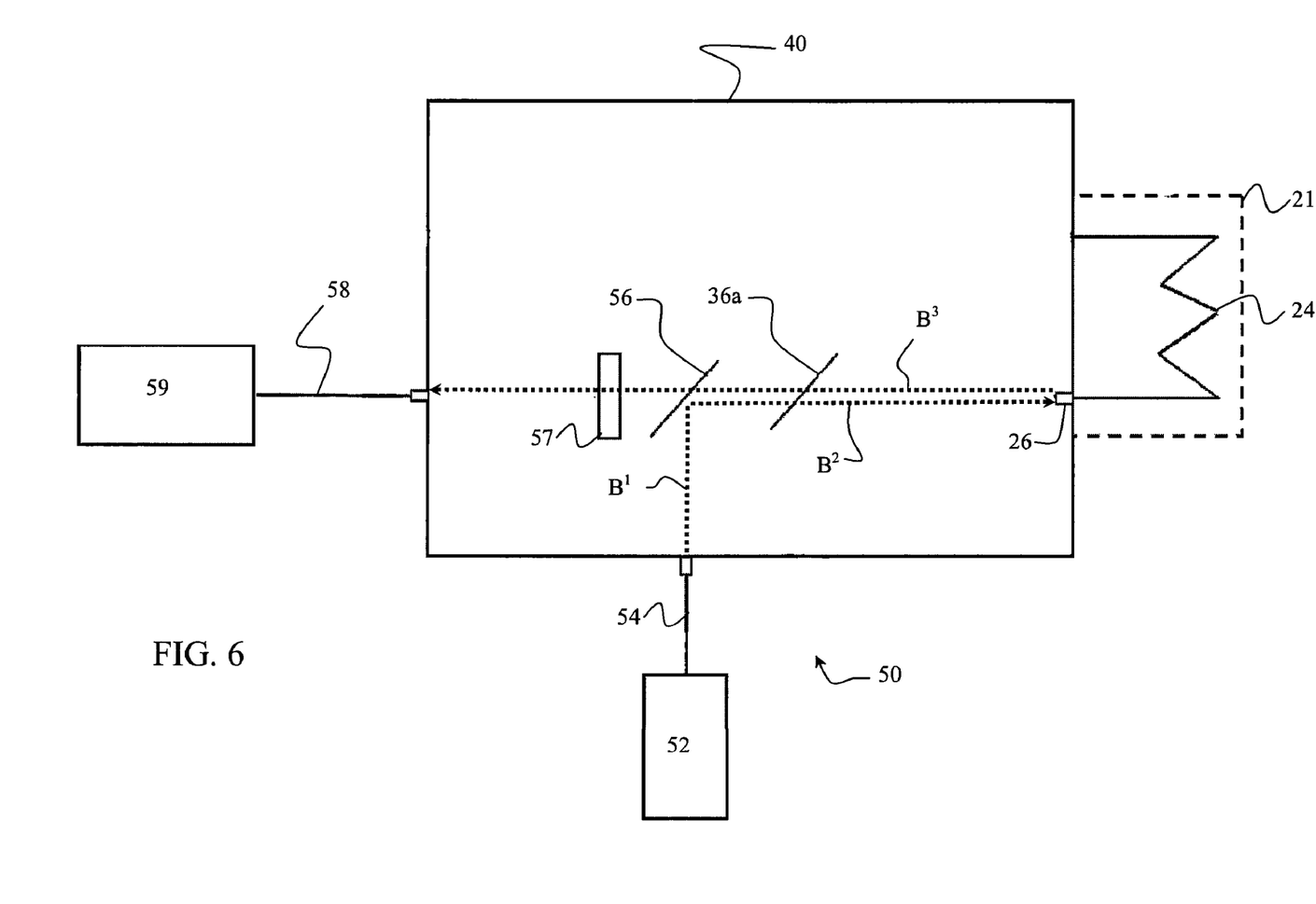
FIG. 6 is a diagram of the Raman subsystem of an illustrative sensing system.

Referring now to FIG. 6, Raman subsystem 50 comprises Raman light source 52 operatively connected to optical platform 40 through Raman source cable 54.

Raman light source 52, in a preferred embodiment, is a frequency-doubled laser which emits 532 nm light but can be any device capable of emitting electromagnetic radiation having a Raman excitation wavelength. As stated above, Optical platform 40 is operatively couple to fiber-optic probe 24 in sample cell 20 through first probe connection 26. Raman spectrometer 59 is operatively connected to optical platform 40 via Raman spectrometer cable 58. Raman source cable 54 and Raman spectrometer cable 58, in a preferred embodiment, each comprise a silica-fiber-optical patch.

Raman subsystem 50 further comprises third optical device 56 and first optical device 36a. Optical filter 57 is disposed between Raman spectrometer 59 and first probe connection 26. Filter 57 is of any type capable of blocking any reflected or scattered light from reaching Raman spectrometer 59. In one embodiment, filter 57 is a holographic notch filter. Third optical device 56 is disposed between filter 57 and first probe connection 26. Optical devices 56 can be any device which controls an optical path of travel. For example, in one embodiment, optical device 56 is a dichroic device which reflects excitation light but transmits Raman scattered light. Optical device 56 can also be a beam splitter, beam combiner or combination thereof. First optical device 36a is disposed between third optical device 56 and first probe connection 26.

In operation, Raman light source emits light through Raman source cable 54 into optical platform 40. The light then travels along first path $B^1$ until contacts third optical device 56 and is redirected along second path $B^2$, thereby defining an optical path, through first optical device 36a and first probe connection 26 into fiber-optic probe 24. The Raman emissions of the sample emanating from first probe connection 26 travel along optical path $B^3$ through first optical device 36a, third optical device 56 and filter 57 to Raman spectrometer 59. The output from Raman spectrometer 59 is fed into an electronic processor for analysis.

Integrated Spectroscopic System

Figure 7:
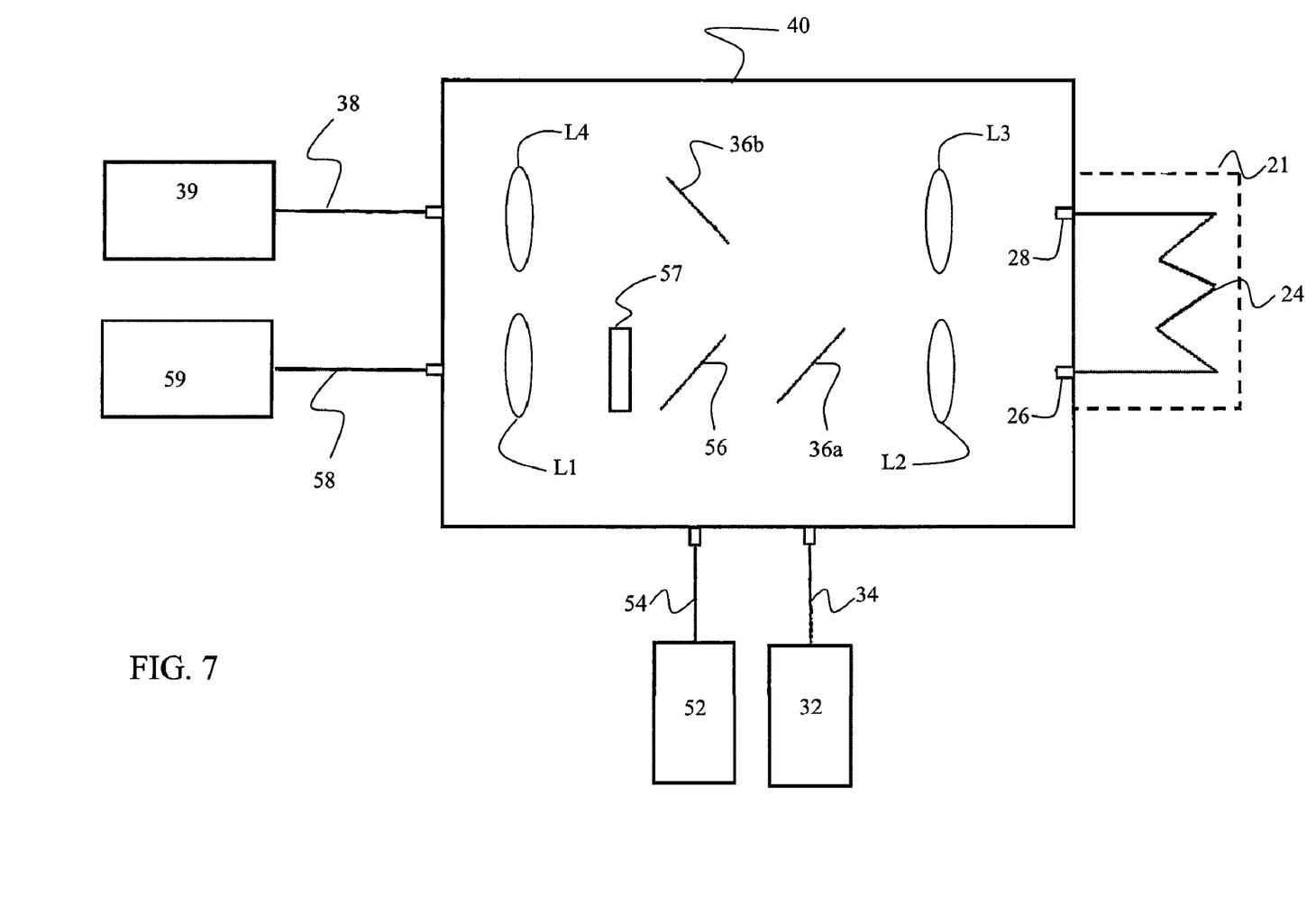
FIG. 7 is a diagram of an illustrative integrated sensing system.

FIG. 7 shows the integrated system and associated optical lens assemblies (L1, L2, L3 and L4) for focusing and collimating combined and separated beams. For example, lens assembly L1 focuses separated Raman scattered light for transmission to Raman spectrometer 59. Lens assembly L2 focuses the combined infrared and excitation beams for transmission to the first probe connection. Lens assembly L3 focuses the infrared emissions from the second probe connection for transmission to the second optical device and lens assembly L4 focuses the separated infrared light for transmission to the infrared spectrometer.

Example II

Figure 8:
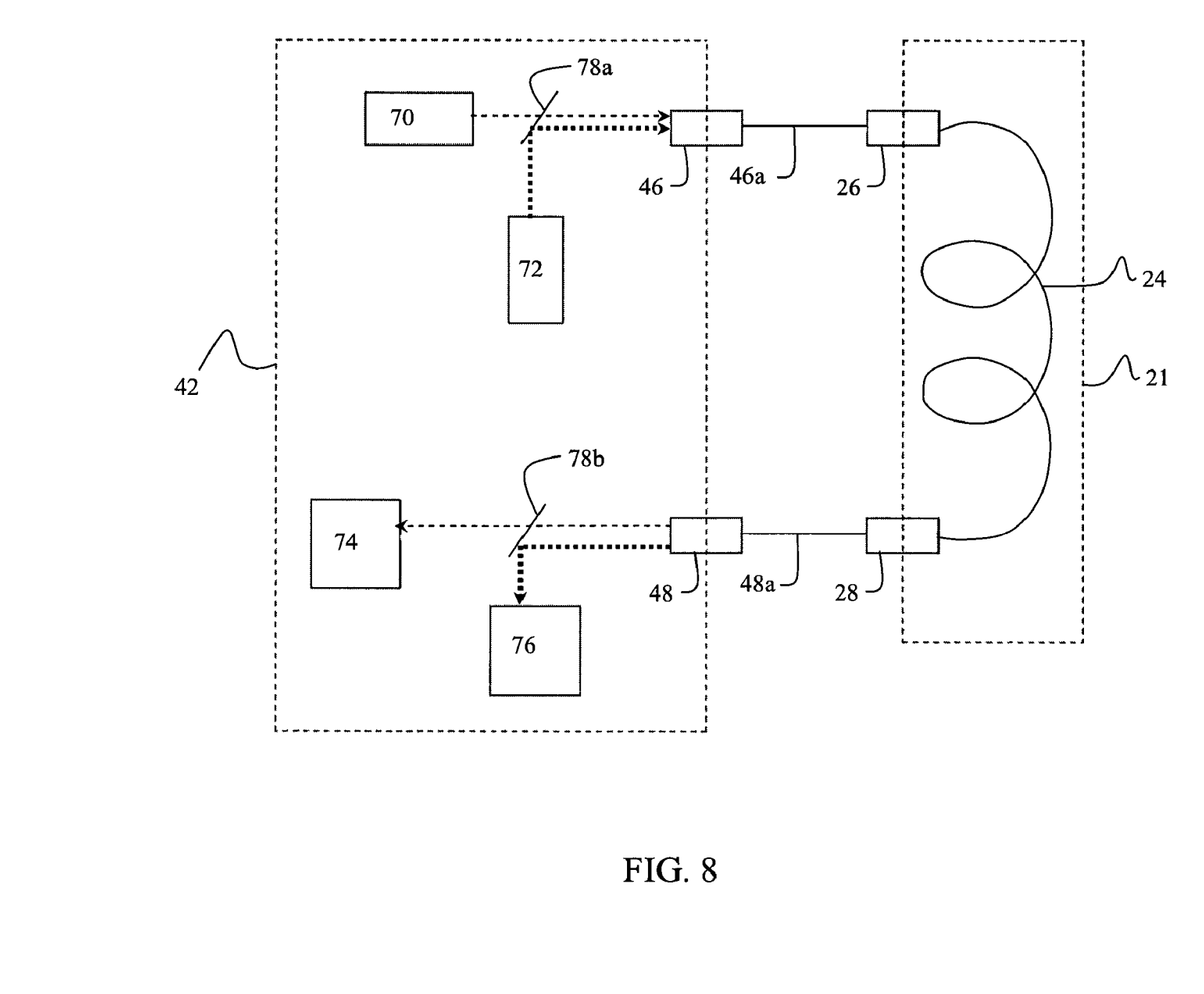
FIG. 8 is a diagram of an alternative integrated sensing system.

An alternate embodiment of the invention is shown in FIG. 8. In this embodiment, optical platform 40 (FIGS. 5-7) is replaced with optical platform 42 which houses first light source 70 and second light source 72. In an illustrative embodiment, first light source 70 is a laser which emits light having wavelength λ used for inducing emission from the sample in sample reactor 20 in which fiber-optic probe 24 is immersed. Second light source 72 is a light source which is a laser which emits light having wavelength $\lambda_2$-$\lambda_3$.

Optical platform 42 is operatively coupled to sample reactor 20 through fiber-optic cables 46a and 48a. First platform connection 46 is operatively connected to first probe connection 26 (via cable 46a) and second platform connection 48 is operatively connected to second probe connection 28 (via cable 48a). Optical platform 42 also comprises first spectrum analyzer 74 for recording the emission excited in the sample by first light source 70 (λ). Second spectrum analyzer 76 records the attenuated light as a result of the evanescent absorption in $\lambda_2$ through $\lambda_3$ wavelengths.

Filter 78a is a dichroic filter with high transmission at λ and high reflection at $\lambda_2$ through $\lambda_3$. Filter 78b is a dichroic filter with high transmission at the wavelength of the induced emission and high reflection at $\lambda_2$ through $\lambda_3$.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A spectroscopic system comprising:
    a fiber-optic probe, comprising an optical fiber having a first end and a second end, adapted to be placed in a fluid sample;
    a first light source optically coupled to the first end of the optical fiber;
    a second light source optically coupled to the first end of the optical fiber;
    a first spectral analyzer optically coupled to the at least one end of the optical fiber; and
    a second spectral analyzer optically coupled to the second end of the optical fiber.

2. The spectroscopic system of claim 1, wherein the fiber-optic probe further comprises:
    a probe body between the first end and the second end; and
    at least one tapered end having a diameter greater than the diameter of the probe body.

3. The spectroscopic system of claim 1, wherein the fiber-optic probe is an unclad fiber.

4. The spectroscopic system of claim 1, wherein the fiber-optic probe has a diameter smaller than about 100 μm.

5. The spectroscopic system of claim 1, wherein the fiber-optic probe is helical.

6. The spectroscopic system of claim 1, wherein the fiber-optic probe is a sapphire fiber.

7. The spectroscopic system of claim 1, wherein the first light source is a laser which emits light selected from the group consisting of light having an excitation wavelength, light having a wavelength of about 532 nm, monochromatic light, near infrared light, ultraviolet light and near ultraviolet light.

8. The spectroscopic system of claim 1, wherein the second light source is a laser which emits light selected from the group consisting of light having a continuously tunable wavelength, incoherent light, near infrared light and infrared light.

9. The spectroscopic system of claim 1, wherein the first spectral analyzer measures light from the first light source that is emitted by the first or second end of the optical fiber of the fiber-optic probe.

10. The spectroscopic system of claim 9, wherein the first spectral analyzer measures Raman scattered light emanating from the sample through the fiber-optic probe.

11. The spectroscopic system of claim 1, wherein the second spectral analyzer measures light from the second light source that is emitted by the second end of the optical fiber of the fiber-optic probe.

12. The spectroscopic system of claim 11, wherein the second spectral analyzer measures the attenuated light emanating from the sample, through the fiber-optic probe, as a result of the evanescent absorption in the infrared wavelengths.

13. The spectroscopic system of claim 11, wherein the second spectral analyzer measures infrared light emanating from the sample through the second end of the fiber-optic probe.

14. The spectroscopic system of claim 1, further comprising:
    a first optical assembly in optical communication between at least one light source and the fiber-optic probe; and
    a second optical assembly in optical communication between at least one spectral analyzer and the fiber-optic probe.

15. The spectroscopic system of claim 14, wherein the first optical assembly is in optical communication between the first light source, the second light source and the first end of the fiber-optic probe.

16. The spectroscopic system of claim 14, wherein the first optical assembly is in optical communication between at least one light source, the fiber-optic probe and the first spectral analyzer.

17. The spectroscopic system of claim 14, wherein first optical assembly is in optical communication between at least one light source and the first end of the fiber-optic probe.

18. The spectroscopic system of claim 14, wherein the second optical assembly is in optical communication between the second spectral analyzer and the second end of the fiber-optic probe.

19. A method of simultaneously measuring absorption and induced emission in a fluid sample, comprising;
    placing a fiber-optic probe, comprising an optical fiber having a first end and a second end, in the fluid sample;
    introducing light from a first light source through the first end of the optical fiber into the sample;
    introducing light from a second light source through the first end of the optical fiber into the sample;
    measuring the light from the first light source emitted by the first or second end of the optical fiber, with a first spectral analyzer; and
    measuring the light from the second light emitted by the second end of the optical fiber, with a second spectral analyzer.

20. The method of claim 19, wherein the fiber-optic probe further comprises:
    a probe body between the first end and the second end; and
    at least one tapered end having a diameter greater than the diameter of the probe body.

21. The method of claim 19, wherein the fiber-optic probe is an unclad fiber.

22. The method of claim 19, wherein the fiber-optic probe has a diameter smaller than about 100 μm.

23. The method of claim 19, wherein the fiber-optic probe is helical.

24. The method of claim 19, wherein the fiber-optic probe is a sapphire fiber.

25. The method of claim 19, wherein the first light source is a laser which emits light selected from the group consisting of light having an excitation wavelength, light having a wavelength of about 532 nm, monochromatic light, near infrared light, ultraviolet light and near ultraviolet light.

26. The method of claim 19, wherein the second light source is a laser which emits light selected from the group consisting of light having a continuously tunable wavelength, incoherent light, near infrared light and infrared light.

27. The method of claim 19, wherein the first spectral analyzer measures Raman scattered light emanating from the sample through the fiber-optic probe.

28. The method of claim 19, wherein the second spectral analyzer measures the attenuated light emanating from the sample, through the fiber-optic probe, as a result of evanescent absorption.

29. The method of claim 19:
    wherein the first spectral analyzer measures the light from the first light source, emitted through the first end of the optical fiber; and
    wherein the second spectral analyzer measures the light from the second light source, emitted through the second end of the optical fiber.

30. The method of claim 19, further comprising:
    providing a first optical assembly in optical communication between at least one light source and the fiber-optic probe; and
    providing a second optical assembly in optical communication between at least one spectral analyzer and the fiber-optic probe.

31. The method of claim 30, wherein the first optical assembly is in optical communication between the first light source, the second light source and the first end of the fiber-optic probe.

32. The method of claim 30, wherein the first optical assembly is in optical communication between at least one light source, the fiber-optic probe and the first spectral analyzer.

33. The method of claim 30, wherein first optical assembly is in optical communication between at least one light source and the first end of the fiber-optic probe.

34. The method of claim 30, wherein the second optical assembly is in optical communication between the second spectral analyzer and the second end of the fiber-optic probe.

* * * * *